(12) United States Patent
Masuda et al.

(10) Patent No.: US 8,030,303 B2
(45) Date of Patent: Oct. 4, 2011

(54) SALT OF MORPHOLINE COMPOUND

(75) Inventors: Katsuhiko Masuda, Tokyo (JP); Shuzo Takeda, Tokyo (JP); Yoshihito Tanaka, Tokyo (JP)

(73) Assignee: Mitsubishi Tanabe Pharma Corporation, Osaka (JP)

( * ) Notice: Subject to any disclaimer, the term of this patent is extended or adjusted under 35 U.S.C. 154(b) by 325 days.

(21) Appl. No.: 12/309,196

(22) PCT Filed: Jul. 11, 2007

(86) PCT No.: PCT/JP2007/063801
§ 371 (c)(1),
(2), (4) Date: Feb. 9, 2009

(87) PCT Pub. No.: WO2008/007691
PCT Pub. Date: Jan. 17, 2008

(65) Prior Publication Data
US 2009/0264430 A1    Oct. 22, 2009

(30) Foreign Application Priority Data
Jul. 11, 2006 (JP) .................................. 2006-190437

(51) Int. Cl.
*A61K 31/535* (2006.01)
*C07D 417/12* (2006.01)
(52) U.S. Cl. ..................................... 514/236.8; 544/133
(58) Field of Classification Search ................ 514/236.8; 544/133
See application file for complete search history.

(56) References Cited

U.S. PATENT DOCUMENTS

| 7,935,700 B2 * | 5/2011 | Tanaka et al. ............. 514/236.8 |
| 2004/0167209 A1 | 8/2004 | Dancer et al. |
| 2007/0265257 A1 * | 11/2007 | Tanaka et al. ............. 514/231.5 |

FOREIGN PATENT DOCUMENTS

| JP | 2005/097120 | 4/2005 |
| JP | 2006/514952 | 5/2006 |
| WO | 2006/028284 | 3/2006 |
| WO | WO 2006/028284 | * 3/2006 |

OTHER PUBLICATIONS

See Bastin, et al., Salt Selection and Optimisation Procedures for Pharmaceutical New Chemical Entities, Organic Process Research & Development, 2000, vol. 4, pp. 427-435, especially p. 428.*
Brittain et al., Polymorphism in Pharmaceutical Solids, vol. 95, 1999, pp. 348-361, esp. p. 348 and 350.*
Soji Awazu et al., Saishin Yakuzaigaku, 7th Edition, 2001, p. 199.
Supplementary European Search Report issued Sep. 17, 2009 in European Application No. 07 79 0605.
S. Petit et al., "The Amorphous State", Polymorphism: in the Pharmaceutical Industry, ed. R. Hilfiker, Wiley-VCH, Weinheim, pp. 259-285, Jan. 1, 2006.

* cited by examiner

*Primary Examiner* — Susannah Chung
(74) *Attorney, Agent, or Firm* — Wenderoth, Lind & Ponack, L.L.P.

(57) ABSTRACT

(2S)-[4-(Carboxymethyl)thiazol-2-ylthio]-N-{[4-(3,4-dichlorobenzyl)morpholin-2-yl]methyl}acetamide hydrobromide and a crystal thereof, which resist easy weight change caused by vapor sorption as compared to a free form, and are superior as drug substances of pharmaceutical products, and a production intermediate therefor are provided.

17 Claims, 5 Drawing Sheets

US 8,030,303 B2

SALT OF MORPHOLINE COMPOUND

This application is a U.S. national stage of International Application No. PCT/JP2007/063801 filed Jul. 11, 2007.

TECHNICAL FIELD

The present invention relates to a salt of (2S)-[4-(carboxymethyl)thiazol-2-ylthio]-N-{[4-(3,4-dichlorobenzyl)morpholin-2-yl]methyl}acetamide and a pharmaceutical use thereof.

BACKGROUND ART (2S)-[4-(Carboxymethyl)thiazol-2-ylthio]-N-{[4-(3,4-dichlorobenzyl)morpholin-2-yl]methyl}acetamide is a compound described in WO WO2006/028284 (patent document 1). This compound is known to show CCR3 affinity, and is useful for the treatment or prophylaxis of acute and chronic inflammatory diseases including immune diseases and allergic diseases, for example, asthma, sinusitis, allergic rhinitis, atopic dermatitis, allergic conjunctivitis, allergic myelitis, ulcerative colitis, Crohn's disease, chronic rheumatoid arthritis and the like.

While patent document 1, Example 2, describes a free form of the aforementioned compound, a specific description of a salt form of the aforementioned compound is not found.
patent document 1: WO WO2006/028284

DISCLOSURE OF THE INVENTION

Problems to be Solved by the Invention

The present invention aims to provide a novel salt form of (2S)-[4-(carboxymethyl)thiazol-2-ylthio]-N-{[4-(3,4-dichlorobenzyl)morpholin-2-yl]methyl}acetamide.

Means of Solving the Problems

In view of the above-mentioned problem, the present inventors have conducted intensive studies and found that (2S)-[4-(carboxymethyl)thiazol-2-ylthio]-N-{[4-(3,4-dichlorobenzyl)morpholin-2-yl]methyl}acetamide hydrobromide (hereinafter sometimes to be abbreviated as the compound of the present invention) is a stable compound that resists easy weight change caused by vapor sorption as compared to its free form, which resulted in the completion of the present invention.

Accordingly, the present invention relates to the following.
(1) (2S)-[4-(Carboxymethyl)thiazol-2-ylthio]-N-{[4-(3,4-dichlorobenzyl)morpholin-2-yl]methyl}acetamide hydrobromide.
(2) A crystal of (2S)-[4-(carboxymethyl)thiazol-2-ylthio]-N-{[4-(3,4-dichlorobenzyl)morpholin-2-yl]methyl}acetamide hydrobromide.
(3) The crystal of (2) showing a powder X-ray diffraction spectrum having a peak at a diffraction angle represented by 2θ of around 24.1° (±0.2°).
(4) The crystal of (2) or (3) showing a powder X-ray diffraction spectrum having a peak at a diffraction angle represented by 2θ of around 25.6° (±0.2°).
(5) The crystal of any one of (2) to (4) showing a powder X-ray diffraction spectrum having a peak at a diffraction angle represented by 2θ of around 22.3° (±0.2°).
(6) The crystal of any one of (2) to (5) showing a powder X-ray diffraction spectrum having a peak at a diffraction angle represented by 2θ of around 20.9° (±0.2°).
(7) The crystal of any one of (2) to (6) showing a powder X-ray diffraction spectrum having peaks at diffraction angles represented by 2θ of around 20.9°, 22.3°, 24.1° and 25.6° (each ±0.2°).
(8) The crystal of any one of (2) to (7) having a melting point (extrapolation-onset temperature) by differential scanning calorimetry of about 163° C. to about 171° C.
(9) The crystal of any one of (2) to (8) having a melting point (extrapolation-onset temperature) by differential scanning calorimetry of about 169° C.
(10) A crystal of (2S)-[4-(carboxymethyl)thiazol-2-ylthio]-N-{[4-(3,4-dichlorobenzyl)morpholin-2-yl]methyl}acetamide hydrobromide having physicochemical properties shown by the following A and/or B:
A: having a powder X-ray diffraction pattern shown in FIG. 1
B: having a differential scanning calorimetry curve shown in FIG. 2.
(11) The crystal of (2) showing a powder X-ray diffraction spectrum having a peak at a diffraction angle represented by 2θ of around 24.9° (±0.2°).
(12) The crystal of any one of (2) and (11) showing a powder X-ray diffraction spectrum having a peak at a diffraction angle represented by 2θ of around 21.7° (±0.2°).
(13) The crystal of any one of (2), (11) and (12) showing a powder X-ray diffraction spectrum having a peak at a diffraction angle represented by 2θ of around 16.0° (±0.2°).
(14) The crystal of any one of (2), (11), (12) and (13) showing a powder X-ray diffraction spectrum having peaks at diffraction angles represented by 2θ of around 16.0°, 21.7° and 24.90 (each ±0.2°).
(15) The crystal of any one of (2), (11), (12), (13) and (14) having a melting point (extrapolation-onset temperature) by differential scanning calorimetry of about 135° C. to about 143° C.
(16) The crystal of any one of (2), (11), (12), (13), (14) and (15) having a melting point (extrapolation-onset temperature) by differential scanning calorimetry of about 141° C.
(17) A crystal of (2S)-[4-(carboxymethyl)thiazol-2-ylthio]-N-{[4-(3,4-dichlorobenzyl)morpholin-2-yl]methyl}acetamide hydrobromide having physicochemical properties shown by the following C and/or D:
C: having a powder X-ray diffraction pattern shown in FIG. 3
D: having a differential scanning calorimetry curve shown in FIG. 4.
(18) An amorphous form of (2S)-[4-(carboxymethyl)thiazol-2-ylthio]-N-{[4-(3,4-dichlorobenzyl)morpholin-2-yl]methyl}acetamide hydrobromide.
(19) An amorphous form of (2S)-[4-(carboxymethyl)thiazol-2-ylthio]-N-{[4-(3,4-dichlorobenzyl)morpholin-2-yl]methyl}acetamide hydrobromide having physicochemical properties shown by the following E:
E: having a powder X-ray diffraction pattern shown in FIG. 5.
(20) A pharmaceutical agent comprising a compound of any of (1) to (19).
(21) A CCR3 antagonist comprising a compound of any of (1) to (19) as an active ingredient.
(22) A pharmaceutical agent comprising a compound of any of (1) to (19) and a pharmaceutically acceptable additive.
(23) The pharmaceutical composition of (22), which is an agent for the prophylaxis and/or treatment of asthma, sinusitis, allergic rhinitis, atopic dermatitis, allergic conjunctivitis, allergic myelitis, ulcerative colitis, Crohn's disease or rheumatoid arthritis.
(24) A (2S)-[4-(carboxymethyl)thiazol-2-ylthio]-N-{[4-(3,4-dichlorobenzyl)morpholin-2-yl]methyl}acetamide potassium salt.

(25) A crystal of (2S)-[4-(carboxymethyl)thiazol-2-ylthio]-N-{[4-(3,4-dichlorobenzyl)morpholin-2-yl]methyl}acetamide potassium salt.
(26) The crystal of claim (25), showing a powder X-ray diffraction spectrum having peaks at diffraction angles represented by 2θ of around 23.1°, 29.8° and 30.7° (each ±0.2°).
(27) A crystal of (2S)-[4-(carboxymethyl)thiazol-2-ylthio]-N-{[4-(3,4-dichlorobenzyl)morpholin-2-yl]methyl}acetamide potassium salt having physicochemical properties shown by the following F:
F: having a powder X-ray diffraction pattern shown in FIG. 6.

Effect of the Invention

It is possible to provide a novel salt form of (2S)-[4-(carboxymethyl)thiazol-2-ylthio]-N-{[4-(3,4-dichlorobenzyl)morpholin-2-yl]methyl}acetamide.

BEST MODE FOR CARRYING OUT THE INVENTION

Figure 1:
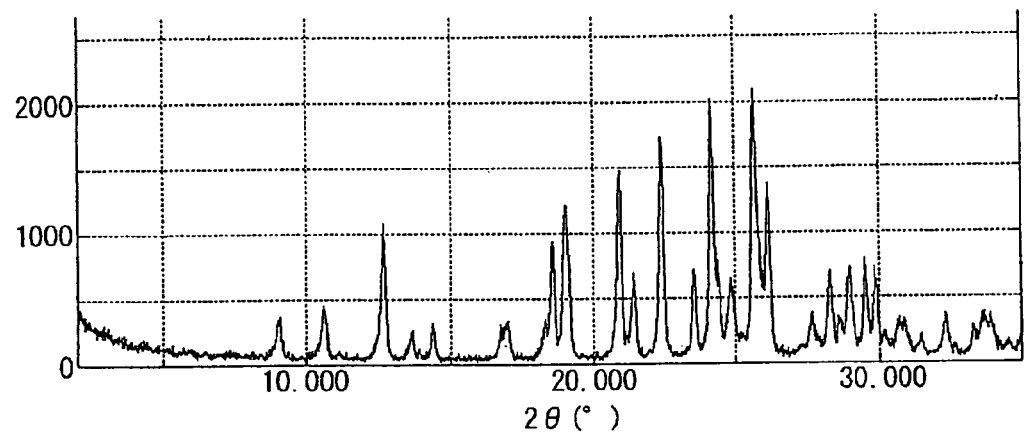
FIG. 1 shows powder X-ray diffraction patterns of compound 1-3.

The present invention provides a novel salt form of (2S)-[4-(carboxymethyl)thiazol-2-ylthio]-N-{[4-(3,4-dichlorobenzyl)morpholin-2-yl]methyl}acetamide of the following formula (I)

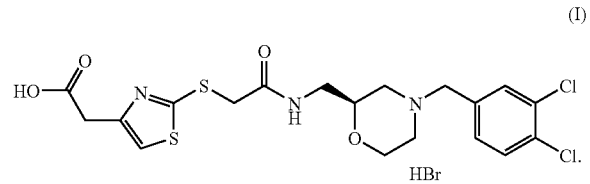

A preferable embodiment of the compound of the present invention is, for example, a crystal of (2S)-[4-(carboxymethyl)thiazol-2-ylthio]-N-{[4-(3,4-dichlorobenzyl)morpholin-2-yl]methyl}acetamide hydrobromide. The crystal (Form I crystal) preferably has a powder X-ray diffraction pattern shown in FIG. 1 and/or a differential scanning calorimetry (DSC) curve shown in FIG. 2. Here, the characteristic peaks in the powder X-ray diffraction pattern are at diffraction angles represented by 2θ of around 20.9°, 22.3°, 24.1° and/or 25.6° (each ±0.2°). The melting point (extrapolation-onset temperature) by DSC is, for example, about 163° C. to about 171° C., preferably about 169° C. As other preferable crystal (Form II crystal) is, for example, a crystal having a powder X-ray diffraction pattern shown in FIG. 3 and/or a DSC curve shown in FIG. 4. Here, the characteristic peaks in the powder X-ray diffraction pattern are at diffraction angles represented by 2θ of around 16.0°, 21.7° and/or 24.9° (each 0.2°). The melting point (extrapolation-onset temperature) by DSC is, for example, about 135° C. to about 143° C., preferably about 141° C. It is possible to provide the compound of the present invention as an amorphous form.

The compounds of the present invention can be obtained, for example, by reacting 1 mol of (2S)-[4-(carboxymethyl)thiazol-2-ylthio]-N-{[4-(3,4-dichlorobenzyl)morpholin-2-yl]methyl}acetamide, which can be produced by a synthetic method described in WO2006/028284, Example 2, with 1 to 10 mol, preferably 1 to 2 mol, more preferably 1 mol, of hydrobromic acid. In addition, it can also be obtained by dissolving an amorphous form of the compound of the present invention in a suitable solvent, for example, acetone, aqueous acetone and the like, which is followed by crystallization. In addition to these, it can also be produced according to the methods shown in the below-mentioned Examples and the like. Furthermore, the compound of the present invention can also be obtained by reacting (2S)-[4-(carboxymethyl)thiazol-2-ylthio]-N-{[4-(3,4-dichlorobenzyl)morpholin-2-yl]methyl}acetamide potassium salt used as a synthetic intermediate or a starting material with an excess amount of hydrobromic acid.

This potassium salt can be obtained as a crystal, and the characteristic peaks in a powder X-ray diffraction pattern expressed as diffraction angles represented by 2θ are around 11.5°, 23.1°, 26.9°, 29.8°, 30.7°, 31.8°, 34.0° and/or 34.5° (each ±0.2°). The characteristic peaks in a powder X-ray diffraction pattern of a compound crystallized from a tetrahydrofuran solvent among the potassium salts are at diffraction angles represented by 2θ of around 23.1°, 29.8° and 30.7° (each ±0.2°).

The compound of the present invention is present as (2S)-[4-(carboxymethyl)thiazol-2-ylthio]-N-{[4-(3,4-dichlorobenzyl)morpholin-2-yl]methyl}acetamide in a solution state, and this compound is known to inhibit the bond between CCR3 and a ligand thereof, and act as an antagonist (WO2006/028284, Table 1 of Experimental Example 1). Accordingly, the compound of the present invention is useful as a CCR3 antagonist, and further useful as a therapeutic drug and/or a prophylactic drug for the diseases in which a cell expressing CCR3 plays a key role in the onset, progress or maintenance of the pathology, for example, asthma, sinusitis, allergic rhinitis, atopic dermatitis, allergic conjunctivitis, allergic myelitis, ulcerative colitis, Crohn's disease, chronic rheumatoid arthritis and the like.

When the compound of the present invention is used as the aforementioned prophylactic and/or therapeutic drug, the compound of the present invention is generally mixed with a pharmaceutically acceptable carrier and can be orally or parenterally administered in the form of a pharmaceutical composition or preparation (e.g., tablet, liquid etc.). The pharmaceutical composition can be formulated according to a general method.

The dose is determined in consideration of age, body weight, general health condition, sex, diet, administration time, administration method, clearance rate, combination of drugs, severity of the disease state of patients under treatment at that time, and other factors. The compound of the present invention is low toxic and can be used safely. While the daily dose of the compound of the present invention varies depending on the condition and body weight of patients, the kind of compound, administration route and the like, for example, oral dose is 0.01 to 1000 mg/kg body weight/day, which is administered in one to several portions a day, and parenteral dose is about 0.001 to 100 mg/kg body weight/day, which is administered in one to several portions a day.

In the present specification, the "prophylactic drug" is a drug to be administered to a healthy individual who has not developed a disease, for example, a drug administered for the object of preventing the onset of a disease. The "therapeutic drug" is a drug to be administered to an individual (patients) who was diagnosed by a doctor to have developed a disease, for example, a drug administered for the object of alleviating a disease or symptom or recovering health. In addition, even if the object of administration is prevention of aggravation of a disease or symptom, or prevention of an attack, when the administration subject is a patient, it is a therapeutic drug.

EXAMPLES

The present invention is explained in detail in the following by referring to Examples and the like, which are not to be construed as limitative.

The chemical shift of $^1$H-NMR is shown by parts per million (ppm) of relative delta (δ) value, using tetramethylsilane (TMS) as the internal standard. The coupling constant is shown in hertz (Hz), and the obvious multiplicity is shown by s (singlet), d (doublet), t (triplet), q (quartet), sept (septet), m (multiplet), dd (doublet of doublets), brs (broad singlet) and the like.

Example 1

Synthesis of (2S)-[4-(carboxymethyl)thiazol-2-ylthio]-N-{[4-(3,4-dichlorobenzyl)morpholin-2-yl]methyl}acetamide hydrobromide (Form I crystal)

1-1 Synthesis of (2S)-N-{[4-(3,4-dichlorobenzyl)morpholin-2-yl]methyl}chloroacetamide (2S)-2-Aminomethyl-4-(3,4-dichlorobenzyl)morpholine dihydrochloride (120 g) was dissolved in tert-butyl methyl ether (450 ml), water (450 ml) was added and the mixture was cooled on an ice bath. Sodium hydrogen carbonate (95.56 g) was gradually added and, after the addition, chloroacetyl chloride (29 ml) was added dropwise over about 10 min while maintaining the inside temperature at 15° C. or below. After the completion of the dropwise addition, the mixture was stirred at room temperature for 1.5 hr. After 1.5 hr, sodium hydrogen carbonate (3 g) and chloroacetyl chloride (2.7 ml) were successively added to the reaction mixture at room temperature, and the mixture was further stirred for 1.5 hr. The reaction mixture was stood still and partitioned, and the organic layer was obtained as a solution of (2S)-N-{[4-(3,4-dichlorobenzyl)morpholin-2-yl]methyl}chloroacetamide in tert-butyl methyl ether.

1-2 Synthesis of (2S)-[4-(carboxymethyl)thiazol-2-ylthio)-N-{[4-(3,4-dichlorobenzyl)morpholin-2-yl]methyl}acetamide (compound 1-2)

4-Ethoxycarbonylmethyl-2-mercaptothiazole (70.14 g) was dissolved in a mixed solution of water (300 ml) and tert-butanol (250 ml), sodium hydroxide (29.46 g) was added on a water bath, and the mixture was stirred for 1.5 hr. To the reaction mixture was added a solution of (2S)-N-{[4-(3,4-dichlorobenzyl)morpholin-2-yl]methyl}chloroacetamide obtained in the above-mentioned 1-1 in tert-butyl methyl ether, and the mixture was stirred at 65° C. for 6 hr. n-Heptane (50 ml) and water (50 ml) were added to the reaction mixture, and the mixture was cooled to room temperature. The reaction mixture was stood still and partitioned, and the aqueous layer was further washed with a mixed solvent of tert-butyl methyl ether (200 ml)/n-heptane (20 ml). 6N Hydrochloric acid (60 ml) was added to the aqueous layer, and the mixture was extracted with ethyl acetate (750 ml) and further extracted twice with a mixed solvent of ethyl acetate (175 ml)/tert-butanol (20 ml). The obtained organic layer was dried over anhydrous sodium sulfate, and the solvent was evaporated under reduced pressure to give a crude product (181 g) of compound 1-2.

1-3 Synthesis of (2 S)-[4-(carboxymethyl)thiazol-2-ylthio]-N-{[4-(3,4-dichlorobenzyl)morpholin-2-yl]methyl}acetamide hydrobromide (compound I-3)

1-3-1: A crude product (181 g) of compound I-2 was dissolved in acetone (800 ml). Insoluble material was separated using a celite filter, and acetone (200 ml) and water (5 ml) were added. Concentrated hydrobromic acid was added. A seed crystal was added, and the mixture was stirred at room temperature for 1 hr, and in an ice bath for 2 hr. The precipitated crystals were collected by filtration, washed with 0.5% aqueous acetone, and dried under reduced pressure to give a crude product (170.6 g) of compound I-3.

1-3-2: A crude product (507.7 g) of compound 1-3 obtained by a method similar to that in 1-3-1 was dissolved in a mixed solvent of acetone (1000 ml) and water (120 ml) with heating at 60° C. Activated carbon (8.2 g) was added and the mixture was stirred at 60° C. for 20 min, and activated carbon was filtered off using a celite filter. The dissolution vessel and filter were washed with a mixed solvent of hot acetone (300 ml) and water (30 ml). The filtrate and washing solution were combined and heated to 40° C., and acetone (3500 ml) was added while maintaining the same temperature. A seed crystal was added, and the mixture was stirred at room temperature for 4 hr. The precipitated crystals were collected by filtration, washed with 1% aqueous acetone, and dried under reduced pressure to give compound 1-3 as white crystals (443.49 g).

$^1$H-NMR (DMSO-$d_6$) δ: 2.77-2.88 (1H, m), 2.98-3.38 (5H, m), 3.65-3.83 (4H, m), 3.96-4.06 (3H, m), 4.34-4.44 (2H, m), 7.39 (1H, s), 7.50-7.56 (1H, m), 7.75-7.79 (1H, m), 7.84-7.87 (1H, m), 8.50 (1H, t, J=5.6 Hz), 10.16 (1H, brs), 12.47 (1H, brs).

Powder X-ray Diffraction (XRD) Analysis

XRD pattern was measured under the following conditions.
apparatus: RINT2200/Ultima+ (Rigaku Corporation)
conditions:
X-ray tube: Cu Kα1
tube current: 40 mA
tube voltage: 40 kV
scan rate: 4°/min
measurement range: 2θ=2 to 35°

The obtained powder X-ray diffraction pattern is shown in FIG. 1.

The characteristic peaks of the crystal were at diffraction angles represented by 2θ of around 20.9°, 22.3°, 24.1° and 25.6° (each ±0.2°).

Differential Scanning Calorimetry (DSC)

Figure 2:
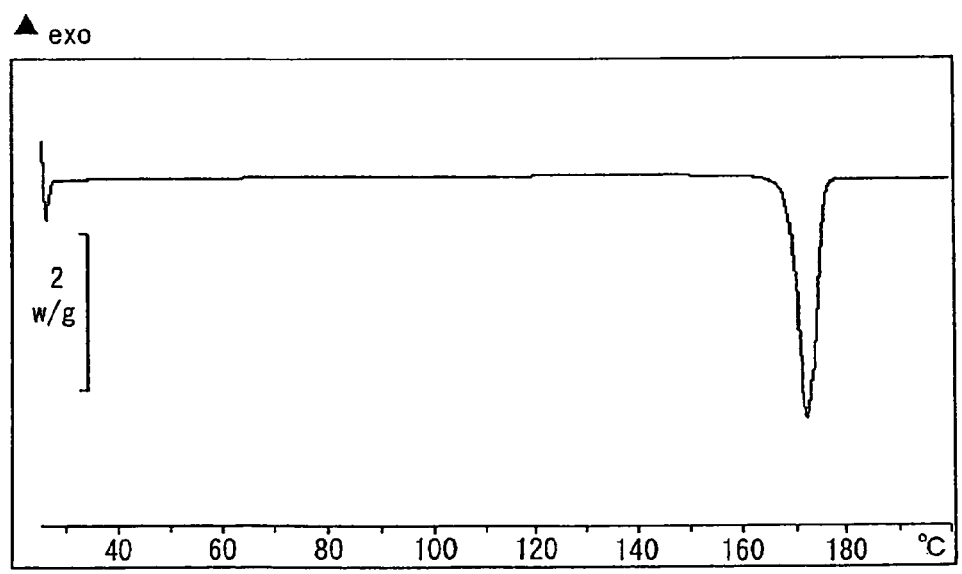
FIG. 2 shows DSC curves of compound 1-3.

The obtained compound (2.8 mg) was set on a differential scanning calorimeter DSC821e (Metttler Toledo Inc.), and measured at a temperature rise rate of 10° C./min (25 to 200° C., nitrogen 40 mL/min). As a result, the melting point (extrapolation-onset temperature) was found at around 169° C. The obtained DSC curve is shown in FIG. 2.

Elemental Analysis

The obtained compound was subjected to elemental analysis to obtain C:39.99, H:3.70, N:7.39, S:11.19, Cl:12.41, Br:13.60 (Calculated; C:39.94, H:3.88, N:7.35, S:11.22, Cl:12.41, Br:13.99).

In addition, compound 1-2 can also be synthesized by the following method.

Synthesis of (2S)-[4-(ethoxycarbonylmethyl)thiazol-2-ylthio]-N-{[4-(3,4-dichlorobenzyl)morpholin-2-yl]methyl}acetamide (compound A)

(2S)-[4-(Ethoxycarbonylmethyl)thiazol-2-ylthio]-N-[(morpholin-2-yl)methyl]acetamide (500 mg) which can be produced according to the method described in WO 06/028284, Example 75, and 3,4-dichlorobenzaldehyde were dissolved in dichloromethane (7 ml), and acetic acid (0.85 ml) was added at room temperature. After stirring at room temperature for 1 hr, sodium triacetoxyborohydride (590 mg) was added to the reaction mixture, and the mixture was stirred at room temperature for 6 hr. Saturated aqueous sodium hydrogen carbonate solution was added to the reaction mixture, and the mixture was extracted with chloroform. The extract was washed with saturated brine, dried over sodium sulfate, and the solvent was evaporated under reduced pressure. The obtained residue was purified by silica gel column chromatography using a mixed solvent of chloroform and methanol as an eluate. The solvent was evaporated from the eluate under reduced pressure to give compound A (360 mg) as a pale-yellow oil.

Synthesis of Compound 1-2

Compound A (350 mg) was dissolved in tetrahydrofuran (1.5 ml) and methanol (1.5 ml). 1M Aqueous sodium hydroxide solution (1.5 ml) was added to the reaction mixture, and the mixture was stirred at room temperature overnight. 1M Hydrochloric acid (2 ml) was added to the reaction mixture, and the organic solvent alone was evaporated under reduced pressure. Water was added to the obtained residue, and the mixture was extracted with chloroform. The extract was washed with saturated brine, dried over sodium sulfate, and the solvent was evaporated under reduced pressure to give compound 1-2 (270 mg) as a colorless amorphous solid.

Example 2

Synthesis of (2S)-[4-(carboxymethyl)thiazol-2-ylthio]-N-{[4-(3,4-dichlorobenzyl)morpholin-2-yl]methyl}acetamide hydrobromide (compound 2) (Form II crystal)

5% Aqueous acetone (4 ml) was added to compound 1-3 (0.34 g) and the mixture was heated under reflux at 60° C. to completely dissolve the compound. The solution was rapidly cooled to 0° C. and a small amount of a seed crystal was added to produce a crystalline white precipitate. The mixture was further stirred at the same temperature for 5 min, and the precipitate was collected by filtration, and dried under reduced pressure at room temperature for 2 hr to give compound 2 (0.18 g) as white crystals.

XRD Analysis

Figure 3:
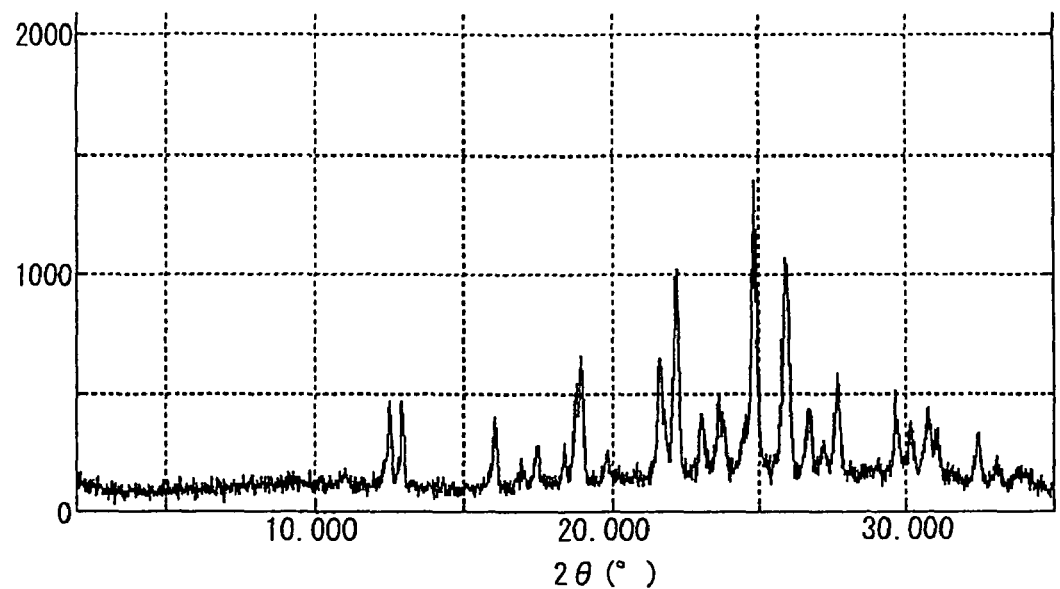
FIG. 3 shows a powder X-ray diffraction pattern of compound 2.

The powder X-ray diffraction pattern obtained by measurement under the same conditions as in the XRD analysis described in Example 1 is shown in FIG. 3. The characteristic peaks of the crystal were at diffraction angles represented by 2θ of around 16.0°, 21.7° and 24.9° (each ±0.2°).

Differential Scanning Calorimetry (DSC)

Figure 4:
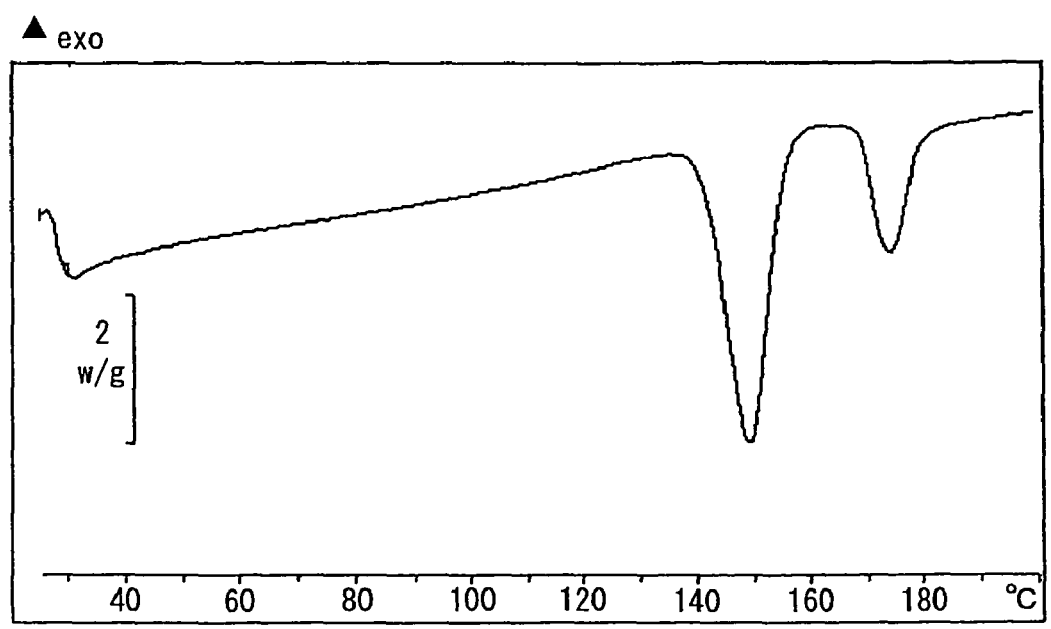
FIG. 4 shows a DSC curve of compound 2.

The obtained compound (1.3 mg) was set on a differential scanning calorimeter DSC821e (Metttler Toledo Inc.), and measured at a temperature rise rate of 40° C./min (25 to 200° C., nitrogen 40 mL/min). As a result, first melting point (extrapolation-onset temperature) was found at about 141° C. The obtained DSC curve is shown in FIG. 4.

Elemental Analysis

The obtained compound was subjected to elemental analysis, and found to be C:39.33, H:3.75, N:7.20, S:11.06, Cl:12.16, Br:13.38 (Calculated; C:39.94, H:3.88, N:7.35, S:11.22, Cl:12.41, Br:13.99).

Example 3

Synthesis of (2S)-[4-(carboxymethyl)thiazol-2-ylthio]-N-{[4-(3,4-dichlorobenzyl)morpholin-2-yl]methyl}acetamide hydrobromide (compound 3) (amorphous form)

Compound 1-3 (2 g) obtained in Example 1 was pulverized in a planetary ball mill pulverizer (type P-7 manufactured by FRITSCH) at 900 rpm for 1 hr to give compound 3 as a white solid.

XRD Analysis

Figure 5:
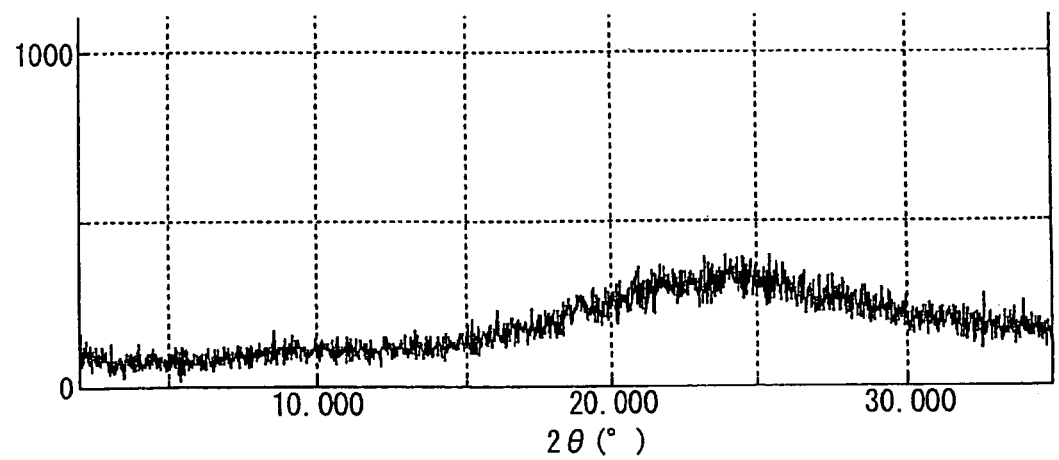
FIG. 5 shows a powder X-ray diffraction pattern of compound 3.

The powder X-ray diffraction pattern obtained by measurement under the same conditions as in the XRD analysis described in Example 1 is shown in FIG. 5. The characteristic peak as a diffraction angle represented by 2θ was not at all observed, but a broad pattern (halo) characteristic of an amorphous form was shown.

Example 4

Synthesis of (2S)-[4-(carboxymethyl)thiazol-2-ylthio]-N-{[4-(3,4-dichlorobenzyl)morpholin-2-yl]methyl}acetamide potassium salt (compound 4)

Compound 1-2 (about 5 mg) obtained according to the method described in WO2006/028284, Example 2, was added to and dissolved in tetrahydrofuran (500 μL), 1.7 mol/L aqueous potassium hydroxide solution (10 μL) was added thereto and the mixture was sufficiently mixed, heated to 40° C., and the solvent was evaporated by itself at room temperature to give a white solid.

XRD Analysis

Figure 6:
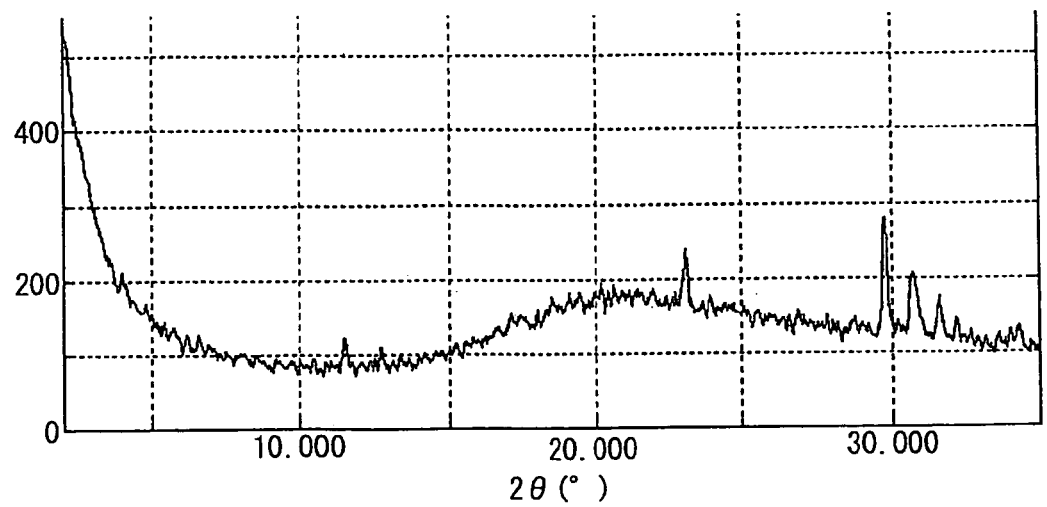
FIG. 6 shows a powder X-ray diffraction pattern of compound 4.

The measurement was performed under the same conditions as in the XRD analysis described in Example 1 except that the scan rate was set to 2°/min. The obtained powder X-ray diffraction pattern is shown in FIG. 6. The characteristic peaks of the crystal were at diffraction angles represented by 2θ of around 23.1°, 29.8° and 30.7° (each ±0.2°).

Experimental Example 1

Vapor Sorption Measurement

A vapor sorption measurement to provide an index of hygroscopicity was performed using a DVS-1 vapor sorption apparatus (manufactured by SMS) under the following conditions. A sample of about 7 mg was used and the relative humidity was increased by 10% within the range of from 0% to 90%, and finally to 95%. The weight change was recorded at each predetermined relative humidity, and the amount of change (%) was calculated based on the weight at relative humidity 0%. As the samples, compound 1-2 (hereinafter to be referred to as a free form) obtained according to the method described in WO 2006/028284, Example 2, compound 1-3 (hereinafter to be referred to as hydrobromide Form I crystal) obtained according to the method described in Example 1 and compound 2 (hereinafter to be referred to as hydrobromide Form II crystal) obtained according to the method described in Example 2 were used.

Figure 7:
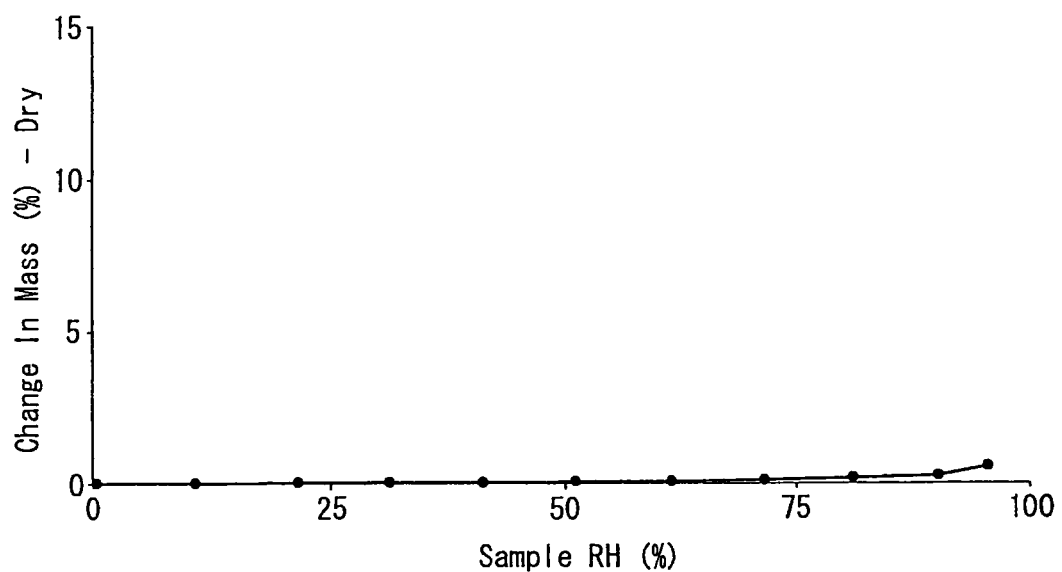
FIG. 7 shows the results of a vapor sorption measurement of the hydrobromide Form I crystal.
Figure 8:
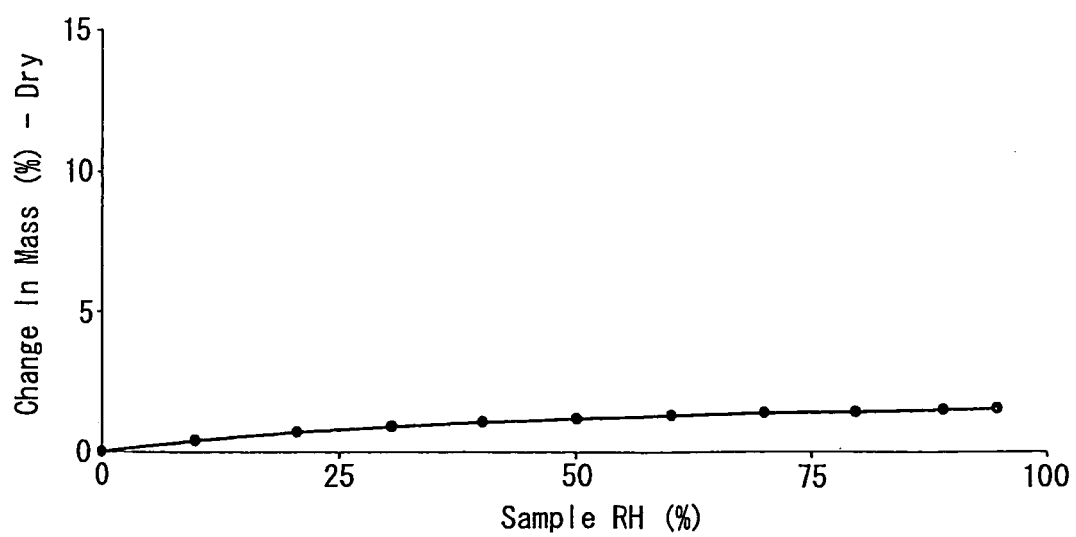
FIG. 8 shows the results of a vapor sorption measurement of the hydrobromide Form II crystal.
Figure 9:
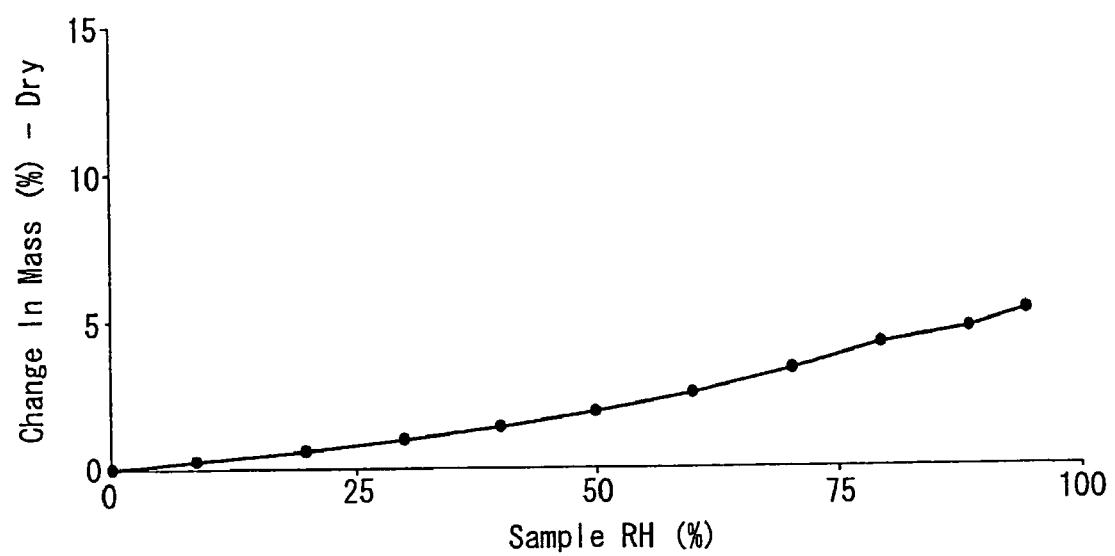
FIG. 9 shows the results of a vapor sorption measurement of the free form.

As a result, as shown in FIGS. 7 to 9, the free form gained weight by 3.3% due to vapor sorption at relative humidity 70% (FIG. 9), and hydrobromide Form I crystal (FIG. 7) and hydrobromide Form II crystal (FIG. 8) showed hygroscopicity only in 0.1% and 1.4% thereof. A small weight change due to humidity is an important factor for the management of the charge amount of a drug substance of pharmaceutical products. It has been clarified that hydrobromide Form I crystal and hydrobromide Form II crystal, which are the crystals of the compound of the present invention, have suitable property as a drug substance of pharmaceutical products.

INDUSTRIAL APPLICABILITY

The crystal of (2S)-[4-(carboxymethyl)thiazol-2-ylthio]-N-{[4-(3,4-dichlorobenzyl)morpholin-2-yl]methyl}acetamide hydrobromide shows small weight change due to humidity and is stable, and is a compound superior as a drug substance of pharmaceutical products.

This application is based on application No. 2006-190437 filed in Japan, the contents of which are incorporated hereinto by reference.

The invention claimed is:

1. A crystal of (2S)-[4-(carboxymethyl)thiazol-2-ylthio]-N-{[4-(3,4-dichlorobenzyl)morpholin-2-yl]methyl}acetamide hydrobromide, showing a powder X-ray diffraction spectrum having peaks at diffraction angles represented by 2θ of around 20.9°, 22.3°, 24.1° and 25.6° (each ±0.2°).

2. A crystal of (2S)-[4-(carboxymethyl)thiazol-2-ylthio]-N-{[4-(3,4-dichlorobenzyl)morpholin-2-yl]methyl}acetamide hydrobromide having physicochemical properties shown by the following A and/or B:
A: having a powder X-ray diffraction pattern shown in FIG. 1
B: having a differential scanning calorimetry curve shown in FIG. 2.

3. A crystal of (2S)-[4-(carboxymethyl)thiazol-2-ylthio]-N-{[4-(3,4-dichlorobenzyl)morpholin-2-yl]methyl}acetamide hydrobromide, showing a powder X-ray diffraction spectrum having peaks at diffraction angles represented by 2θ of around 16.0°, 21.7° and 24.9° (each ±0.2°).

4. A crystal of (2S)-[4-(carboxymethyl)thiazol-2-ylthio]-N-{[4-(3,4-dichlorobenzyl)morpholin-2-yl]methyl}acetamide hydrobromide having physicochemical properties shown by the following C and/or D:
C: having a powder X-ray diffraction pattern shown in FIG. 3
D: having a differential scanning calorimetry curve shown in FIG. 4.

5. An amorphous form of (2S)-[4-(carboxymethyl)thiazol-2-ylthio]-N-{[4-(3,4-dichlorobenzyl)morpholin-2-yl]methyl}acetamide hydrobromide having physicochemical properties shown by the following E:
E: having a powder X-ray diffraction pattern shown in FIG. 5.

6. A CCR3 antagonist comprising a compound of claim 2 as an active ingredient.

7. A CCR3 antagonist comprising a compound of claim 4 as an active ingredient.

8. A CCR3 antagonist comprising a compound of claim 5 as an active ingredient.

9. A crystal of (2S)-[4-(carboxymethyl)thiazol-2-ylthio]-N-{[4-(3,4-dichlorobenzyl)morpholin-2-yl]methyl}acetamide potassium salt, showing a powder X-ray diffraction spectrum having peaks at diffraction angles represented by 2θ of around 23.1°, 29.8° and 30.7° (each ±0.2°).

10. A crystal of (2S)-[4-(carboxymethyl)thiazol-2-ylthio]-N-{[4-(3,4-dichlorobenzyl)morpholin-2-yl]methyl}acetamide potassium salt having physicochemical properties shown by the following F:
F: having a powder X-ray diffraction pattern shown in FIG. 6.

11. A CCR3 antagonist comprising a compound of claim 1 as an active ingredient.

12. A CCR3 antagonist comprising a compound of claim 3 as an active ingredient.

13. A method for the treatment of asthma, sinusitis, allergic rhinitis, atopic dermatitis, allergic conjunctivitis, allergic myelitis, ulcerative colitis, Crohn's disease or rheumatoid arthritis, which comprises administering an effective amount of the compound of claim 1 to a patient in need thereof.

14. A method for the treatment of asthma, sinusitis, allergic rhinitis, atopic dermatitis, allergic conjunctivitis, allergic myelitis, ulcerative colitis, Crohn's disease or rheumatoid arthritis, which comprises administering an effective amount of the compound of claim 2 to a patient in need thereof.

15. A method for the treatment of asthma, sinusitis, allergic rhinitis, atopic dermatitis, allergic conjunctivitis, allergic myelitis, ulcerative colitis, Crohn's disease or rheumatoid arthritis, which comprises administering an effective amount of the compound of claim 3 to a patient in need thereof.

16. A method for the treatment of asthma, sinusitis, allergic rhinitis, atopic dermatitis, allergic conjunctivitis, allergic myelitis, ulcerative colitis, Crohn's disease or rheumatoid arthritis, which comprises administering an effective amount of the compound of claim 4 to a patient in need thereof.

17. A method for the treatment of asthma, sinusitis, allergic rhinitis, atopic dermatitis, allergic conjunctivitis, allergic myelitis, ulcerative colitis, Crohn's disease or rheumatoid arthritis, which comprises administering an effective amount of the compound of claim 5 to a patient in need thereof.

* * * * *